(12) United States Patent
Kanai et al.

(10) Patent No.: US 11,021,461 B2
(45) Date of Patent: Jun. 1, 2021

(54) ARTIFICIAL CATALYST SYSTEM FOR SELECTIVE ACYLATION OF CHROMOSOME PROTEIN

(71) Applicant: THE UNIVERSITY OF TOKYO, Tokyo (JP)

(72) Inventors: Motomu Kanai, Tokyo (JP); Shigehiro Kawashima, Tokyo (JP); Kenzo Yamatsugu, Tokyo (JP); Yoshifumi Amamoto, Tokyo (JP); Yuki Aoi, Tokyo (JP); Hiroki Suto, Tokyo (JP); Nozomu Nagashima, Tokyo (JP); Hitoshi Kurumizaka, Tokyo (JP); Akihisa Osakabe, Tokyo (JP); Yasuhiro Arimura, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 3 days.

(21) Appl. No.: 15/755,938

(22) PCT Filed: Aug. 29, 2016

(86) PCT No.: PCT/JP2016/075183
§ 371 (c)(1),
(2) Date: Jul. 24, 2018

(87) PCT Pub. No.: WO2017/038760
PCT Pub. Date: Mar. 9, 2017

(65) Prior Publication Data
US 2019/0047985 A1   Feb. 14, 2019

(30) Foreign Application Priority Data
Aug. 28, 2015   (JP) .............................. JP2015-169448

(51) Int. Cl.
| | | |
|---|---|---|
| A61P 35/00 | (2006.01) | |
| C07D 401/14 | (2006.01) | |
| C07K 1/13 | (2006.01) | |
| A61K 45/06 | (2006.01) | |
| A61K 31/4439 | (2006.01) | |
| A61K 31/16 | (2006.01) | |

(52) U.S. Cl.
CPC ........ *C07D 401/14* (2013.01); *A61K 31/4439* (2013.01); *A61K 45/06* (2013.01); *A61P 35/00* (2018.01); *C07K 1/13* (2013.01); *A61K 31/16* (2013.01); *A61K 2300/00* (2013.01)

(58) Field of Classification Search
CPC ........................................................ A61P 35/00
See application file for complete search history.

(56) References Cited

FOREIGN PATENT DOCUMENTS

| WO | 2010/001933 A1 | 1/2010 |
|---|---|---|
| WO | 2012/100176 A2 | 7/2012 |
| WO | 2015/186785 A1 | 12/2015 |
| WO | 2016/129680 A1 | 8/2016 |

OTHER PUBLICATIONS

Amamoto, Y., et al. "Synthetic Posttranslational Modifications: Chemical Catalyst-Driven Regioselective Histone Acylation of Native Chromatin." Journal of American Chemical Society. (2017), vol. 139, pp. 7568-7576. (Year: 2017).*
Hangxiang Wang, et al., "Chemical Cell-Surface Receptor Engineering Using Affinity-Guided, Multivalent Organocatalysts", Journal of the American Chemical Society, 2011, pp. 12220-12228, vol. 133.
Yoichiro Koshi, et al., "Target-Specific Chemical Acylation of Lectins by Ligand-Tethered DMAP Catalysts", Journal of the American Chemistry Society, 2008, pp. 245-251, vol. 130.
Hiroshi Sugiyama, "Histone Deacetylase Sogai Kassei o Motsu Pyrrole-Imidazole Polyamide ni yoru Tokutei Idenshi no Kasseika", Research Reports of Uehara Memorial Foundation, 2009, pp. 1 to 5, p. 1, columns of 'Introduction', 'Method and Result'.
James E. Brownell, et al., "Tetrahymena Histone Acetyltransferase A: A Homolog to Yeast Gcn5p Linking Histone Acetylation to Gene Activation", Cell, Mar. 22, 1996, pp. 843-851, vol. 84.
V. M. Richon, et al., "Second generation hybrid polar compounds are potent inducers of transformed cell differentiation", Proc. Natl. Acad. Sci. USA, Jun. 1996, pp. 5705-5708, vol. 93.
Laura Pasqualucci, et al., "Inactivating mutations of acetyltransferase genes in B-cell lymphoma", Nature, 2011, pp. 189-195, vol. 471.
Zhongyu Xie, et al., "Lysine Succinylation and Lysine Malonylation in Histones", Molecular & Cellular Proteomics, 2011, pp. 100-107, vol. 11, No. 5.
Chao Peng, et al., "The First Identification of Lysine Malonylation Substrates and Its Regulatory Enzyme", Molecular & Cellular Proteomics, 2011, 10.1074/mcp.M111.012658-1-10.1074/mcp.M111.012658-12, vol. 10.
Minjia Tan, et al., "Lysine Glutarylation is a Protein Post-Translational Modification Regulated by SIRT5", Cell Metabolism, 2014, vol. 19, pp. 605-617.
Yue Chen, et al., "Lysine Propionylation and Butyrylation are Novel Post-translational Modifications in Histones", Molecular & Cellular Proteomics, 2007, pp. 812-819, vol. 6.
Lunzhi Dai, et al.,"Lysine 2-hydroxyisobutyrylation is a widely distributed active histone mark", Nature Chemical Biology, 2014, vol. 10, pp. 365-370.
J. Steven Stanley, et al., "Biotinylation of histones in human cells", Eur. J. Biochem., 2001, pp. 5424-5429, vol. 268.
International Search Report for PCT/JP2016/075183 dated Nov. 8, 2016 [PCT/ISA/210].

* cited by examiner

*Primary Examiner* — John S Kenyon
(74) *Attorney, Agent, or Firm* — Sughrue Mion, PLLC

(57) ABSTRACT

An artificial catalyst system which can acylate chromosome proteins with high selectivity has successfully been established by using a combination of an acyl CoA activating catalyst having target acylation area binding ability and acyl CoA or a derivative thereof.

2 Claims, 9 Drawing Sheets

Fig. 5

| Histone | Residue | Yield (%) | Enzyme | Histone | Residue | Yield (%) | Enzyme |
|---|---|---|---|---|---|---|---|
| H2A | K5 | <0.5 | t | H2B | K5 | <2.0 | t |
|  | K9 | <0.5 | t |  | K11 | <2.0 | t |
|  | K13 | 0.4 | t |  | K12 | <2.0 | t |
|  | K15 | 1.0 | t |  | K15 | <2.0 | t |
|  | K36 | <0.5 | t |  | K16 | <2.0 | t |
|  | K74 | <0.5 | t |  | K20 | <2.0 | t |
|  | K75 | <0.5 | t |  | K23 | <2.0 | t |
|  | K95 | 0.4 | t |  | K24 | <2.0 | t |
|  | K118 | <2.0 | c |  | K27 | <2.0 | t |
|  | K119 | <2.0 | c |  | K28 | <2.0 | t |
|  | K125 | <5.0 | c |  | K30 | ND |  |
|  | K127 | <5.0 | c |  | K34 | ND |  |
|  | K129 | <5.0 | c |  | K43 | ND |  |
|  |  |  |  |  | K46 | <2.0 | c |
|  |  |  |  |  | K57 | <2.0 | c |
|  |  |  |  |  | K85 | <1.0 | t |
|  |  |  |  |  | K108 | 2.9 | c |
|  |  |  |  |  | K116 | 1.3 | c |
|  |  |  |  |  | K120 | 54.4 | c |
|  |  |  |  |  | K125 | ND |  |

| Histone | Residue | Yield (%) | Enzyme | Histone | Residue | Yield (%) | Enzyme |
|---|---|---|---|---|---|---|---|
| H3 | K4 | ND |  | H4 | K5 | ≤1.2 | t |
|  | K9 | <0.5 | t |  | K8 | ≤1.2 | t |
|  | K14 | <0.5 | t |  | K12 | ≤1.2 | t |
|  | K18 | <0.5 | t |  | K16 | ≤1.2 | t |
|  | K23 | <0.5 | t |  | K20 | ND |  |
|  | K27 | ≤1.1 | t |  | K31 | 0.3 | t |
|  | K36 | ≤1.1 | t |  | K44 | <5.0 | c |
|  | K37 | ≤1.1 | t |  | K59 | <0.5 | t |
|  | K56 | <0.5 | t |  | K77 | <0.5 | t |
|  | K64 | <0.5 | t |  | K79 | <0.5 | t |
|  | K79 | <0.5 | t |  | K91 | <0.5 | t |
|  | K115 | <5.0 | c |  |  |  |  |
|  | K122 | <0.5 | t |  |  |  |  |

| Determination Method |
|---|
| Method A |
| Method B |
| Method C |

| Enzyme |
|---|
| t: Trypsin |
| c: Chymotrypsin |

Fig. 6

| Histone | Residue | Yield (%) | Enzyme | Histone | Residue | Yield (%) | Enzyme |
|---|---|---|---|---|---|---|---|
| H2A | K5 | < 0.5 | t | H2B | K5 | < 10 | t |
|  | K9 | < 0.5 | t |  | K11 | < 10 | t |
|  | K13 | ND | t |  | K12 | < 10 | t |
|  | K15 | ND | t |  | K15 | < 10 | t |
|  | K36 | 1.5 | t |  | K16 | ND |  |
|  | K74 | < 0.5 | t |  | K20 | ND |  |
|  | K75 | < 0.5 | t |  | K23 | < 0.5 | t |
|  | K95 | 0.8 | t |  | K24 | < 0.5 | t |
|  | K118 | 1.0 | c |  | K27 | < 0.5 | t |
|  | K119 | 3.6 | c |  | K28 | < 0.5 | t |
|  | K125 | < 0.5 | c |  | K30 | ND |  |
|  | K127 | < 0.5 | c |  | K34 | ND |  |
|  | K129 | < 0.5 | c |  | K43 | < 5 | t |
|  |  |  |  |  | K46 | < 1 | c |
|  |  |  |  |  | K57 | < 1 | c |
|  |  |  |  |  | K85 | < 0.5 | t |
|  |  |  |  |  | K108 | < 0.5 | t |
|  |  |  |  |  | K116 | < 0.5 | t |
|  |  |  |  |  | K120 | < 0.5 | t |
|  |  |  |  |  | K125 | < 5 | t |

| Histone | Residue | Yield (%) | Enzyme | Histone | Residue | Yield (%) | Enzyme |
|---|---|---|---|---|---|---|---|
| H3 | K4 | ND |  | H4 | K5 | < 0.5 | t |
|  | K9 | 2.1 | t |  | K8 | < 0.5 | t |
|  | K14 | 2.4 | t |  | K12 | < 0.5 | t |
|  | K18 | < 0.5 | t |  | K16 | < 0.5 | t |
|  | K23 | < 0.5 | t |  | K20 | ND |  |
|  | K27 | 2.0 | t |  | K31 | 1.8 | t |
|  | K36 | 14.1 | t |  | K44 | ND |  |
|  | K37 | 1.9 | t |  | K59 | < 0.5 | t |
|  | K56 | 8.9 | t |  | K77 | 13.7 | t |
|  | K64 | < 0.5 | t |  | K79 | < 0.5 | t |
|  | K79 | < 0.5 | t |  | K91 | < 0.5 | t |
|  | K115 | ND |  |  |  |  |  |
|  | K122 | < 0.5 | t |  |  |  |  |

| Determination Method |
|---|
| Method A |
| Method B |
| Method C |

| Enzyme |
|---|
| t: Trypsin |
| c: Chymotrypsin |

ARTIFICIAL CATALYST SYSTEM FOR SELECTIVE ACYLATION OF CHROMOSOME PROTEIN

CROSS REFERENCE TO RELATED APPLICATIONS

This application is a National Stage of International Application No. PCT/JP2016/075183 filed Aug. 29, 2016, claiming priority to Japanese Patent Application No. 2015-169448 filed August.

TECHNICAL FIELD

The present invention relates to an artificial catalyst system substitutable for an in vivo acylation function, and particularly to an artificial catalyst system for selective acylation of chromosome proteins.

BACKGROUND ART

In vivo post-translational modifications of proteins play key roles in regulations of biological functions. Post-translational modifications include various reactions such as methylation and phosphorylation, and a typical example thereof includes histone acetylation. Histones are main proteins composing a chromosome, and have a role in storing DNA in the nucleus, the DNA being wound around the histones. Besides, histones are actively involved in dynamic regulations of chromosome structure and gene transcriptions following acetylation of lysine residues in histones with a histone acetyltransferase, and deacetylation thereof with a histone deacetylase (NPL 1).

Enhancing histone acetylation leads to gene transcription enhancement. Accordingly, anticancer agents have been developed which inhibit histone deacetylases and thereby promote the transcription of a tumor suppressor gene. A typical example thereof includes Zolinza, a drug against cutaneous T cell lymphoma (NPL 2).

Many small molecule drugs, which are for treatment of diseases, exhibit their efficacy by controlling, particularly inhibiting, the functions of endogenous enzymes of the organisms. However, an approach using a small molecule drug with such actions has a problem that the therapeutic effect cannot be expected in a case where a disease is caused by a loss or inactivation of an enzyme itself. For example, an endogenous histone acetyltransferase is inactivated in some B-cell lymphomas. For this reason, it is concerned that acetylation enhancement cannot be expected from a treatment with a histone deacetylase inhibitor (NPL 3).

Furthermore, recently, malonylation, succinylation, glutarylation, butyrylation, 2-hydroxy-iso-butyrylation, and biotinylation have been found out as the other acylation modifications on histones than acetylation. It has been suggested that these modifications play important roles in the structure and function and the like of histones (NPL 4 to 9).

CITATION LIST

Non Patent Literature

[NPL 1] Brownell, J. E. et al., Cell, 1996, 84, 843-851
[NPL 2] Richon, V. M. et al., Proc. Natl. Acad. Sci. USA, 1996, 93, 5705-5708
[NPL 3] Pasqualucci, L. et al., Nature, 2011, 471, 189-195
[NPL 4] Xie, Z. et al., Mol Cell Proteomics, 2012 May; (5), 100-107
[NPL 5] Peng, C. et al., Molecular & Cellular Proteomics 2011, 10, M111.012658
[NPL 6] Tan, M. J. et al., Cell Metabolism 2014, 19, 605-617
[NPL 7] Chen, Y. et al., Molecular & Cellular Proteomics 2007, 6, 812-819
[NPL 8] Dai, L. Z. et al., Nature Chemical Biology 2014, 10, 365-370
[NPL 9] Stanley, J. S., Griffin, J. B. & Zempleni, J., European Journal of Biochemistry 2001, 268, 5424-5429

SUMMARY OF INVENTION

Technical Problem

Cells are a place where integrated chemical reactions take place, and life activities are supported by the activity of enzymes, one type of catalysts. Thus, if an artificial catalyst system substitutable for in vivo enzyme functions can be developed, the system will enable effective treatments against diseases caused by a loss or inactivation of an enzyme as described above. Accordingly, an object of the present invention is to develop an artificial catalyst system substitutable for an in vivo enzyme function, and to realize a medical treatment based on a novel concept of "catalysis medicine" in which the system is introduced into cells.

As an example of this "catalysis medicine," an object of the present invention is to provide an artificial catalyst system substitutable for an in vivo acylation function. The present invention aims particularly to provide an artificial catalyst system which is capable of selective acylation of chromosome proteins.

Solution to Problem

In order to achieve the above objects, the present inventors first made investigation for various acetylating agents on the selectivity of the acetylation of cytoplasm proteins. As a result, it was revealed that while EG5-PTA and N-methoxydiacetamide (NMD) non-selectively acetylated a large quantity of protein, acetyl CoA being an acetyl group donor used by organisms and TEG-Ac being an analog thereof did not cause non-selective acetylation (FIG. 1B). This fact means that if a catalyst capable of activating low reactivity acetyl group donors with suppressed non-selective reaction such as acetyl CoA is developed, it is possible to construct an artificial catalyst system capable of acetylation with high selectivity.

In light of this, the present inventors have made earnest studies on catalysts capable of activating acetyl CoA and have at last come up with an idea of an acetyl CoA activation mechanism using a novel catalyst DMAP-SH (hereinafter sometimes abbreviated to"DSH") (FIG. 2). In this mechanism, thiol groups introduced into DSH perform thiol-thioester exchange reaction with thioester groups of acetyl CoA. Thereby, DSH takes acetyl groups in the catalyst molecules, and activates the acetyl groups through intramolecular reaction. Here, the present inventors considered that the target site could be acetylated with high selectivity by further introducing, into DSH, molecules having binding ability to a specific area on the chromosome and causing the DSH to bind to a peripheral area of the target site.

In light of the above, catalysts (referred to as "LANA-DSH" and "PIP-DSH") were synthesized by introducing pyrrole-imidazole polyamide (PIP) (Dervan, P. B., Bioorganic & Medicinal Chemistry 2001, 9, 2215-2235) being a DNA sequence specifically recognizing binding molecule and LANA (Barbera, A. J. et al., Science 2006, 311, 856-861) being a histone protein binding molecule. The feasibility of the idea described above was tested by use of these.

First, as a result of the evaluation on the protein selectivity, it was revealed that histone selective acetylation was possible by using LANA-DSH or PIP-DSH (FIG. 3A). Also in the case of performing an experiment using, instead of acetyl CoA, a derivative which was a cutout portion of acetyl CoA, histone selective acetylation was similarly observed.

Next, as a result of the evaluation on the selectivity among lysine residues in histones, it was revealed that LANA-DSH particularly acetylated the 120th lysine residue of Histone H2B (H2BK120), and that PIP-DSH particularly acetylated the 36th lysine residue (H3K36) and the 56th lysine residue (H3K56) of Histone H3, and 77th lysine residue of Histone H4 (H4K77) (FIGS. 3B, 5, and 6). These acetylation sites were in the neighborhood of the binding site of LANA and PIP on the nucleosome derived from an X-ray crystal structure (FIGS. 7 and 8). From the above findings, it was demonstrated that the target site could be acetylated with high selectivity by combining acetyl CoA and DSH to which a molecule having binding ability to the target acetylation area was introduced.

Furthermore, the present inventors performed tests using various acyl CoA other than acetyl CoA as an acyl group donor to be combined with the catalysts described above, and as a result found out that it was possible to selectively perform various acylations other than acetylations such as malonylation, glutarylation, butyrylation, 2-hydroxy-iso-butyrylation, and biotinylation (FIG. 9).

In sum, the present invention relates to a novel acyl CoA activating catalyst having binding ability to a target acylation area (hereinafter referred to as a "target acylation area binding catalyst") and to a high selectivity chromosome protein acylation system which uses a combination of the catalyst and acyl CoA or a derivative thereof. More specifically, the following is provided.

(1) A compound comprising the following structure:

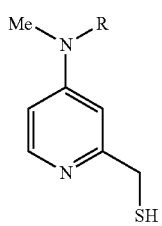

[Chem. 1]

(R represents any molecule having binding ability to a target acylation area)

(2) A drug for acylation of a chromosome protein, comprising a combination of the compound described in (1) and acyl CoA or a derivative thereof.

Advantageous Effects of Invention

The present invention provides a high selectivity chromosome protein acylation system which uses a combination of a target acylation area binding catalyst and acyl CoA or a derivative thereof. It was itself very epoch-making and surprising that the function of an enzyme, which is exhibited through e.g. interaction with other proteins in vivo, could be substituted with such an artificial catalyst system.

In the artificial catalyst system of the present invention, an acetylation site can be freely selected at an amino acid residue level simply by altering target acylation area binding molecules to be introduced into the catalyst. In addition, using the same catalyst, it is possible to perform various acylations including acetylation, malonylation, and the like in the target site simply by altering the type of acyl CoA or a derivative thereof to be combined. Hence, it can be said that the artificial catalyst system of the present invention is a system highly versatile and excellently practical.

Since the acylation derived by the artificial catalyst system of the present invention is independent of in vivo enzymes, the system makes it possible to provide novel medical treatment with a mechanism of action essentially different from those of conventional pharmaceuticals targeted for in vivo enzymes. This makes it possible to pave the way toward medical treatment targeted even for patients for whom no therapeutic effects can be observed with conventional pharmaceuticals in the treatment of, for example, diseases attributed to abnormal acylation of chromosome proteins.

BRIEF DESCRIPTION OF DRAWINGS

FIG. 5 is a diagram illustrating results of exhaustively detecting acetylation of a reconstituted nucleosome by the catalyst (LANA-DSH) of the present invention.

FIG. 6 is a diagram illustrating results of exhaustively detecting acetylation of a reconstituted nucleosome by the catalyst (PIP-DSH) of the present invention.

DESCRIPTION OF EMBODIMENTS

<Target Acylation Area Binding Catalyst>

Figure 1:
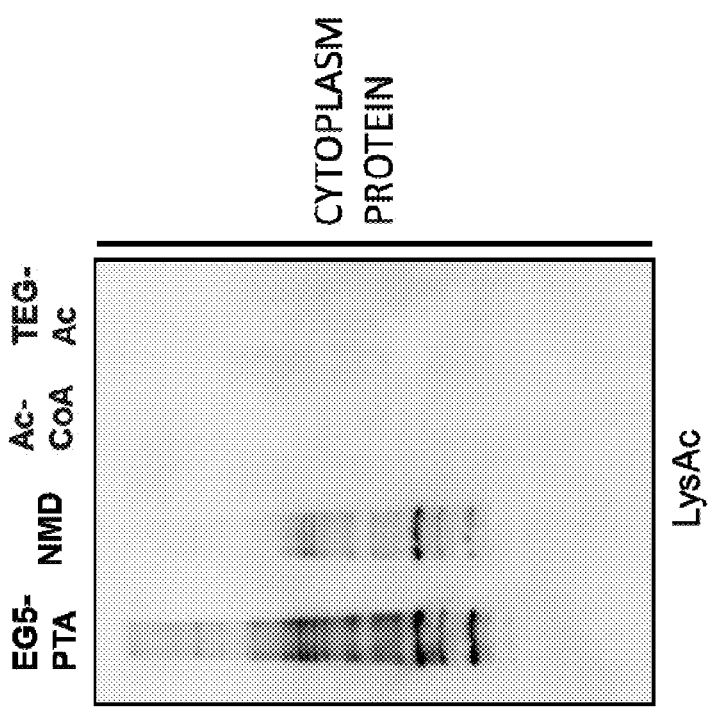
FIG. 1 is a diagram illustrating structures of acetyl group donors and reactivity comparison. "A" illustrates the structures of the acetyl group donors, and "B" is a photo indicating comparison of reactivity of the acetyl group donors with cytoplasm proteins.
Figure 1:
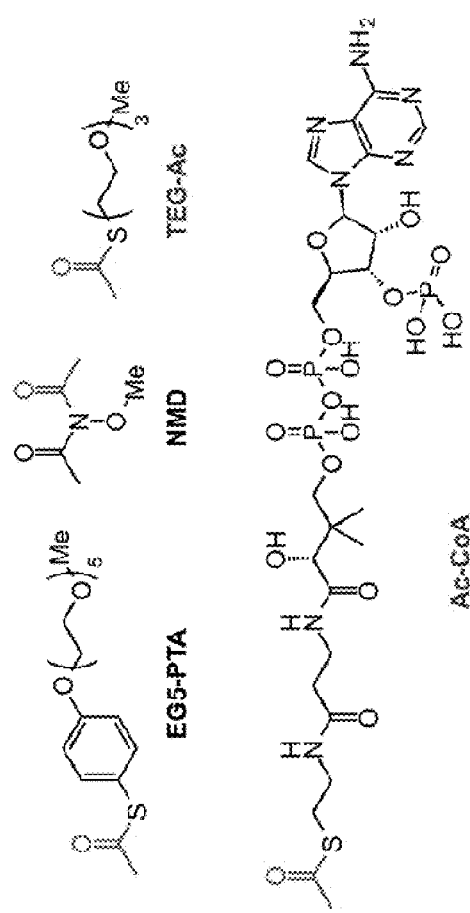

The present invention provides a target acylation area binding catalyst, specifically a compound comprising the following structure:

[Chem. 2]

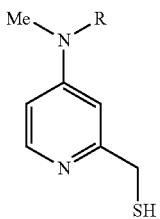

(R represents any molecule having binding ability to a target acylation area)

The target acylation area binding catalyst of the present invention is a constituting element of the artificial catalyst system of the present invention, and is capable of acylation of proteins with high selectivity when combined with acyl CoA or a derivative thereof.

In the present invention, "acylation" means the introduction of an acyl group into a functional group having substitutable hydrogen atoms. For example, the acylation in the present invention is, but is not limited to, acetylation, malonylation, glutarylation, butyrylation, 2-hydroxy-iso-butyrylation, and biotinylation.

In the present invention, a "target acylation area" means a target acylation site and a peripheral area thereof. Here, the "peripheral area" means an area which is, when the catalyst of the present invention binds, close to the target acylation site to such a degree that causes acylation reaction in the target acylation site. Whether or not the synthesized catalyst has binding ability to the peripheral area of the target acylation site may be evaluated by, for example, a method described in the present Example in terms of whether or not the synthesized catalyst acylates the target acylation site.

If the target acylation site is present in a particular chromosome protein, the catalyst of the present invention may bind to a chromosome DNA present in the peripheral area of the target acylation site, may bind to a chromosome protein present in the peripheral area of the target acylation site, or may bind to both of them.

Since any molecules having binding ability to the target acylation area can be introduced into the target acylation area binding catalyst of the present invention, it is possible to provide more than one target acylation area depending on the structure of the molecule.

In the case of introducing molecules having binding ability to a target acylation area into a target acylation area binding catalyst, the introduction may be carried out with a linker. The linker is not particularly limited as long as it does not inhibit binding ability to the target acylation area of the target acylation area binding catalyst to be synthesized and activation ability of acyl CoA or a derivative thereof.

Two examples of the target acylation area binding catalyst of the present invention are shown below.

[Chem. 3]

(1)

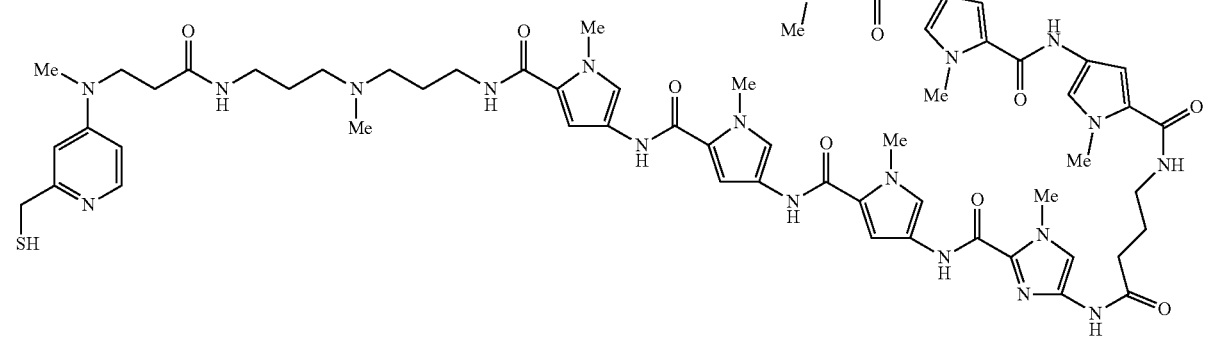

PIP-DSH (2)

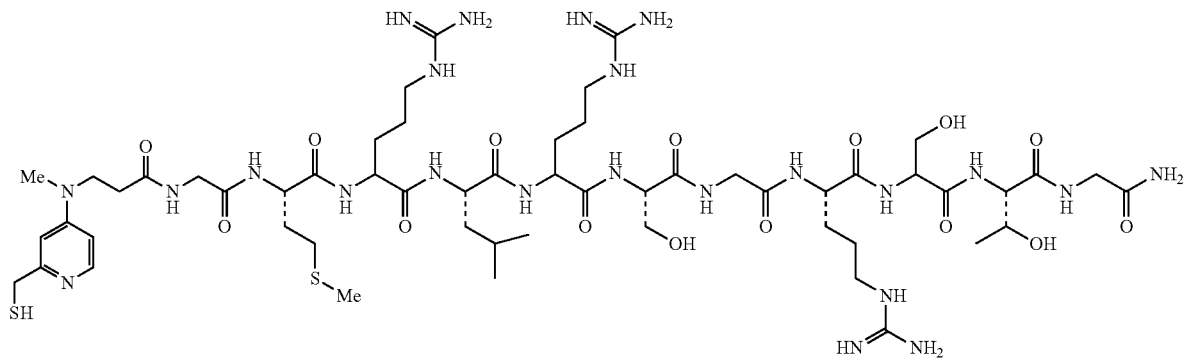

LANA-DSH

PIP-DSH is an aspect of the catalyst of the present invention which binds to chromosome DNA. The PIP is a DNA sequence specifically recognizing binding molecule, and is capable of giving any base sequence specificity by properly disposing pyrrole and imidazole in a molecular structure. Thus, it is possible to perform efficient acylation in the target acylation site by molecular design of the PIP based on the base sequence on the chromosome DNA present in the peripheral area of the target acylation site and by introducing it into the catalyst of the present invention. In the PIP-DSH used in the present Example, the 36th lysine residue (H3K36) and the 56th lysine residue (H3K56) of Histone H3, and the 77th lysine residue of Histone H4 (H4K77) were particularly acylated. It should be understood by those skilled in the art that acylation is possible with other lysine residues as targets by appropriately changing the positions of pyrrole and imidazole in the PIP.

Figure 7:
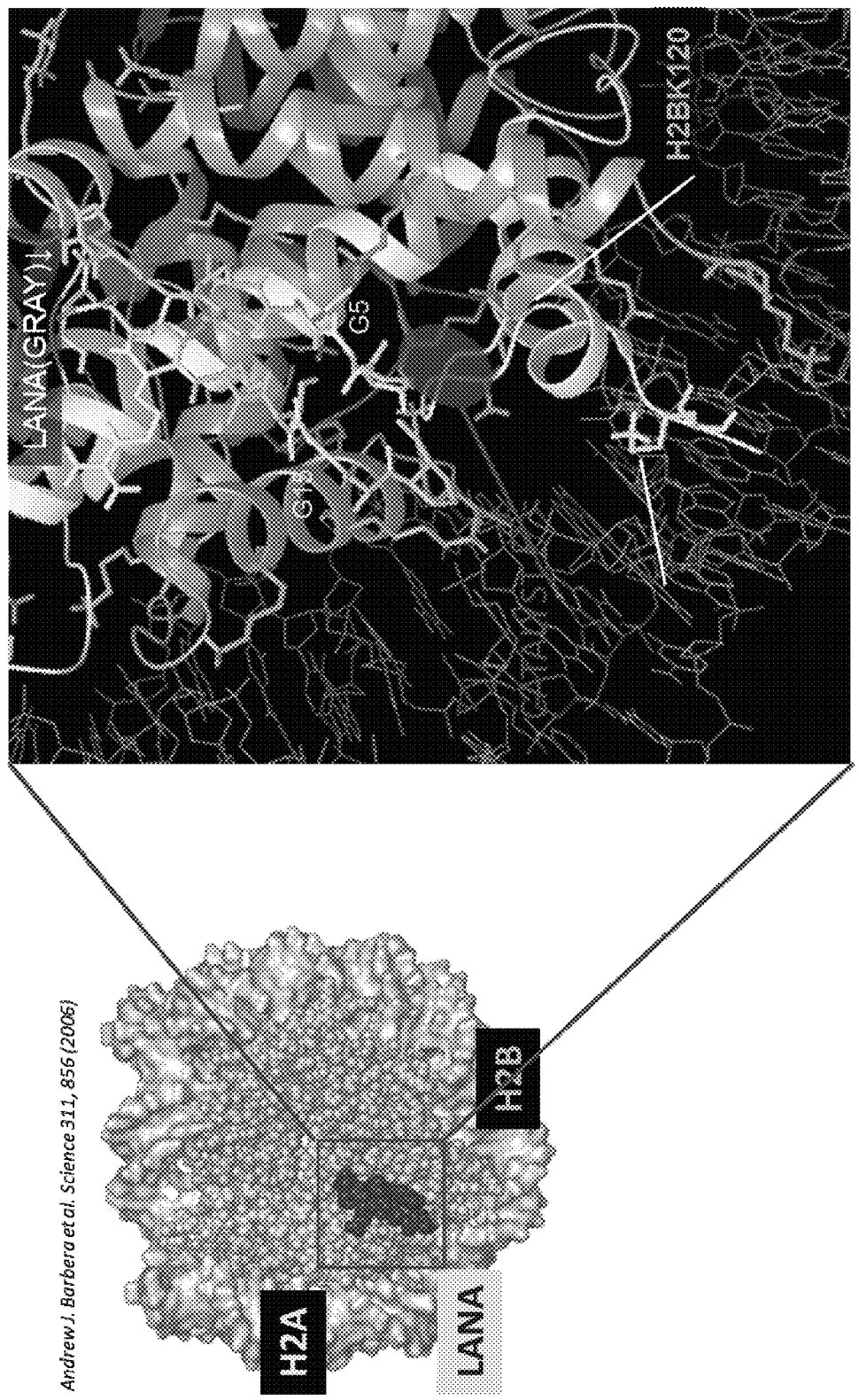
FIG. 7 is a diagram illustrating an X-ray crystal structure indicating localization of LANA used for the catalyst (LANA-DSH) of the present invention on the nucleosome.

On the other hand, LANA-DSH is an aspect of the catalyst of the present invention which binds to chromosome proteins. LANA is a histone protein binding molecule, and an N-terminus area thereof binds to an H2A-H2B dimer of chromatin (FIG. 7). Thus, by introducing LANA into the catalyst of the present invention, it is possible to acylate the acylation site present around the biding site described above, particularly the 120th lysine residue of Histone H2B (H2BK120).

For example, one may think of using peptide nucleic acids (PNA), aptamers, or guide RNAs of CRISPR-Cas9 systems as molecules having biding ability to a target acylation area, other than those described above. The peptide nucleic acids (PNA) are molecules which form chains complementary to DNA bases and bind DNA in a DNA sequence specific manner (Hyrup B. & Nielsen P. E., Bioorganic & Medicinal Chemistry 1996, 1, 5-23). The aptamers are DNA or RNA chains having a three-dimensional structure which binds to a target, and DNA aptamers which bind to histone tails have been reported (Hanyang Yu, et al., ChemBioChem 2011, 12, 2659-2666). The guide RNAs of the CRISPR-Cas9 systems form a pair of complementary chain bases with target DNA and thereby bind to a target in a DNA sequence specific manner (Hsu P. D. et al., Cell 2014, 157, 1262-1278). By introducing these molecules into the catalyst of the present invention, various sites in the chromosome protein can be an acylation target.

Figure 2:
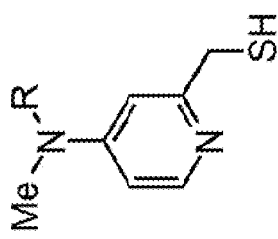
FIG. 2 is a diagram illustrating a basic structure of a catalyst (DSH) of the present invention and a reaction mechanism thereof. "A" illustrates a basic structure of the catalyst (DSH) of the present invention, and "B" illustrates an expected activation mechanism of acetyl CoA by DSH.
Figure 2:
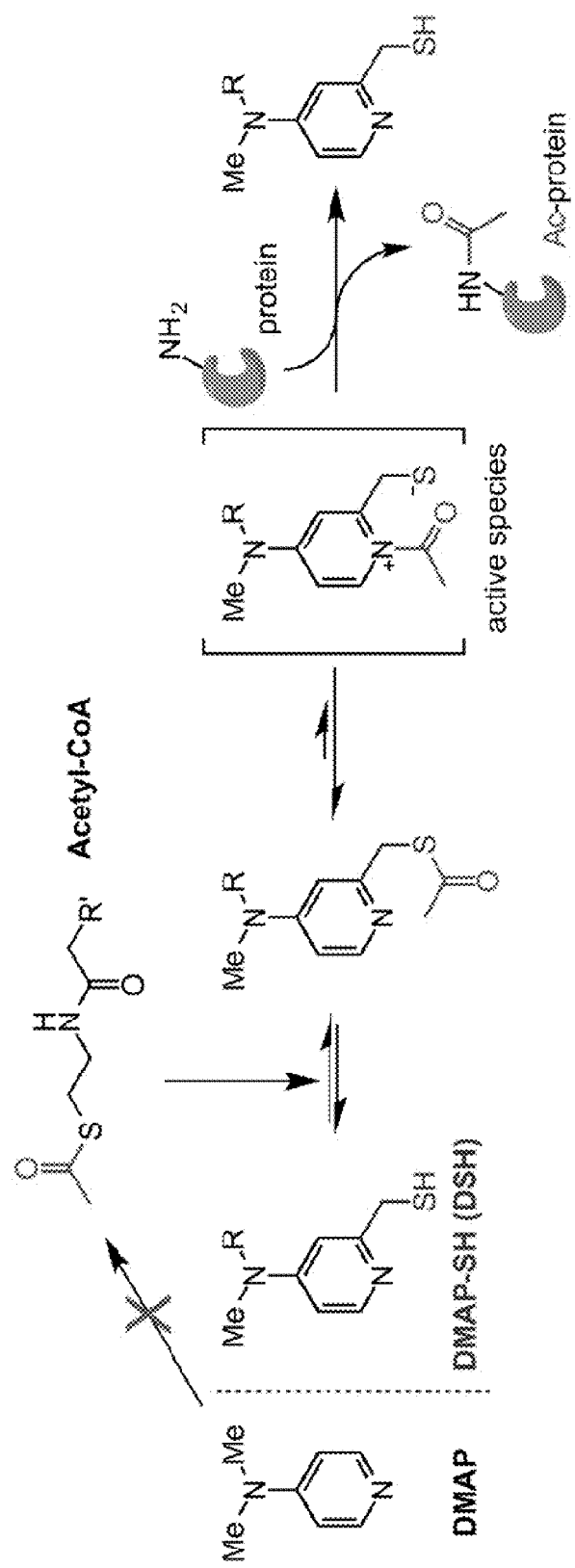
Figure 9:
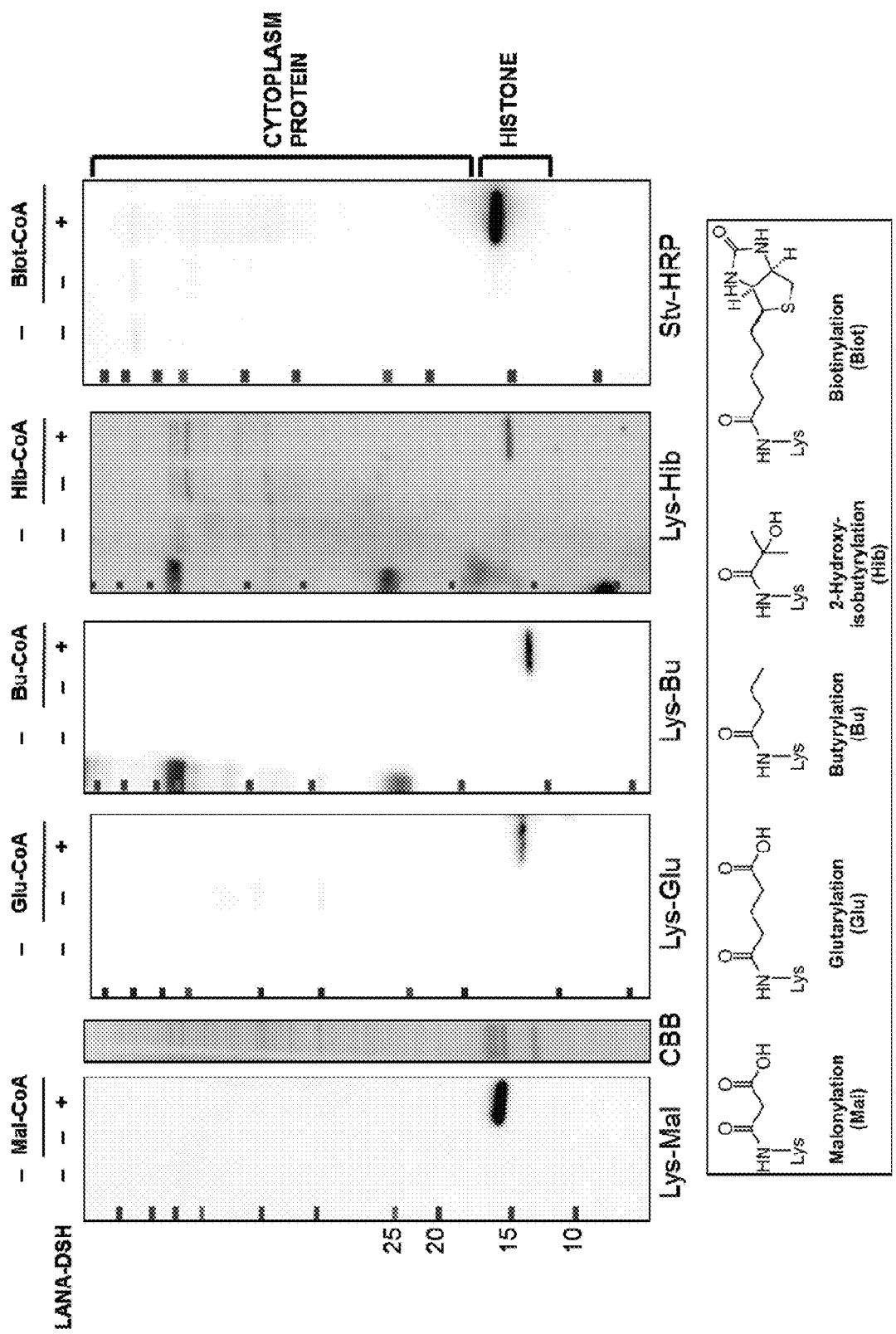
FIG. 9 is a diagram illustrating results of analyzing abilities to acylate by the catalyst (LANA-DSH) of the present invention. The figures above each are a photo indicating results of detecting various acylations, and the figure below illustrates structures of lysine residues after the various acylations.

In the target acylation area binding catalyst of the present invention, the introduced thiol groups cause thiol-thioester exchange reaction with the thioester groups of acetyl CoA to take the acetyl groups in the catalyst molecules, and activates the acetyl groups through intramolecular reaction (FIG. 2). This activation mechanism also makes it possible to activate various acyl CoA other than acetyl CoA (FIG. 9).

<Combination Agent>

The present Example has revealed that it is possible to acylate chromosome proteins with the combination of the target acylation area binding catalyst and acyl CoA or a derivative thereof. Thus, the present invention provides a drug for acylation of a chromosome protein comprising the above-described combination of the target acylation area binding catalyst and acyl CoA or a derivative thereof. In addition, the present invention provides a method of acylating a chromosome protein which uses the combination.

Here, the "derivative of acyl CoA" is a compound in which the structure of acyl CoA is partially modified, and means a compound which functions as an acyl group donor by being activated by the target acylation area binding catalyst. The derivative of acyl CoA typically has the following structure.

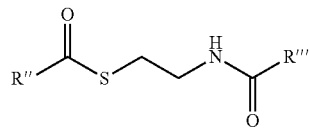

[Chem. 4]

Here, R" and R'" represent any substituent. R" is a substituent constituting an acyl group and may be selected as appropriate depending on the type of acylation intended. R'" is not particularly limited as long as it does not inhibit the function of the compound described above as an acyl group donor when activated by the target acylation area binding catalyst.

An example of the acyl CoA derivative (acetyl CoA derivative) used in the present Example is shown below.

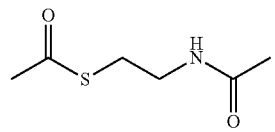

[Chem. 5]

The present Example has proven that the acetyl CoA derivative functions as an acetyl group donor as in the case of acetyl CoA. This fact indicates that the degree of freedom of the structure of R'" is high when functioning as an acyl group donor.

The "chromosome proteins" to be acylated are mainly histones (for example, Histones H3 and H4). As described above, it is possible to theoretically design the target acylation area binding catalyst of the present invention depending on the target acylation site, and to cause the catalyst to have specificity to various sites on the chromosome. Thus, the catalyst can be used for acylation of chromosome proteins other than histones.

The acylation of lysine residues of the chromosome proteins can be evaluated by, for example, a western blotting method which uses an anti-acylated lysine antibody (refer to the "Western Blotting" item in "Materials and Methods"). In the case of evaluating the acylation of particular lysine residues (for example, H3K56 and H4K77), one may use an antibody specific to the acylated particular lysine residues.

The drug of the present invention can be used as a reagent for acylation of chromosome proteins and as a pharmaceutical for the treatment of a disease and the like attributed to the decrease in acylation of chromosome proteins.

Since the relationship between the acylation (in particular, acetylation) of chromosome proteins and cancer is known, the "disease attributed to the decrease in acylation of chromosome proteins" is preferably cancer. Since an endogenous histone acetyltransferase is inactivated in some B-cell lymphomas, it is concerned that acetylation enhancement cannot be expected from a treatment with a histone deacetylase inhibitor (Pasqualucci, L. et al., Nature 2011, 471, 189-195). According to the drug of the present invention, even in the case where the endogenous histone acetyltransferase is inactivated, it is possible to complement the function thereof, and to exhibit an efficacy which cannot be exhibited by conventional histone deacetylase inhibitors.

In addition, the drug of the present invention may be used in combination with other anticancer agents and other cancer treatment methods (for example, radiation therapy and immunotherapy). It has been suggested that histone acetylation decondenses the chromatin structure, thereby increases the DNA accessibility and enhances the sensitivity of chromosome DNA to a DNA-damaging agent and radiation (Oleinick et al., Int. J. Radiat. Biol. 1994, 66, 523-529, Gorisch S M, et al., J Cell Sci 2005, 118, 5825-5834, Camphausen K, et al. Int J Cancer 2005, 114, 380-366, Karagiannis TC & El-Osta A. Oncogene 2006, 25, 3885-3893, Kim M S, et al., Exp Cell Res 2005, 306, 94-102, Kim M S, et al., Cancer Res 2003, 63, 7291-7300, Piacentini P, et al., Virchows Arch 2006, 448, 797-804). Since the drug of the present invention is believed to act on chromosome proteins to decondense the chromatin structure of the target site, synergistic effects can also be expected from the combination with a DNA targeting agent (for example, an anticancer agent having a DNA-damaging action) or a DNA-targeting treatment method (for example, radiation therapy).

The drug of the present invention may be combined with a complement for enhancing therapeutically useful characteristics. Examples of typical useful characteristics thereof include: promoting the delivery of the compounds to a target site (for example, tumor), keeping the therapeutic window of the compounds in a target site, modifying the pharmacokinetic characteristics and pharmacodynamic characteristics of the compounds, and improving the therapeutic index or safety profile of the compounds.

In a case where the drug of the present invention is used as a pharmaceutical, the target acylation area binding catalyst and acyl CoA or a derivative thereof can be formulated as active ingredients by known pharmaceutical methods. The phrase that the drug of the present invention "comprises a combination" of the target acylation area binding catalyst and acyl CoA or a derivative thereof means that the drug of the present invention may be in the form of a single agent comprising both of the target acylation area binding catalyst and acyl CoA or a derivative thereof as active ingredients, or may be in the form of concomitant agents of a preparation comprising the target acylation area binding catalyst as an active ingredient and a preparation comprising the acyl CoA or a derivative thereof as an active ingredient.

Examples of a pharmacologically acceptable carrier used in the formulation include sterile water, physiological saline, vegetable oils, solvents, bases, emulsifiers, suspensions, surfactants, stabilizers, flavors, aromatic substances, excipients, vehicles, antiseptics, binders, diluents, isotonic agents, soothing agents, bulking agents, disintegrators, buffers, coating agents, lubricants, colorants, sweeteners, viscous agents, flavor modifiers, solubilizers, other additives, and the like, but are not limited thereto. The active ingredients can be made in various forms such as tablets, powders, granules, capsules, and liquids, in accordance with the purpose of the treatment and so forth. Moreover, the active ingredients can also be administered in the form of liposome delivery system. To the liposome, the aforementioned complements (such as, for example, antibody and ligand) can also be added to enhance therapeutically useful characteristics.

The administration to a patient can be carried out by either oral administration or parenteral administration. Examples of the parenteral administration include intravenous administration, intraarterial administration, intramuscular administration, intrathoracic administration, intraperitoneal administration, direct administration to a target site (for example, tumor), and the like. In the case where the agent of the present invention is concomitant agents, the preparations may be administered at the same time, or may be administered at different timings such that the combination effect will not be reduced.

The dose is not particularly limited, as long as the amount is effective for treating a target disease, and should be selected as appropriate in accordance with the age, weight, symptom, and health state of a patient, the progression of the disease, and so forth. How often the agent is administered is not particularly limited, either, and can be selected as appropriate in accordance with the purpose. For example, as the dose administered in a day, the agent may be administered once a day, or may be administered separately multiple times a day. When the agent of the present invention is administered to human, the range of the dose of the active ingredients per day is normally approximately 0.01 mg/kg body weight to approximately 500 mg/kg body weight, preferably approximately 0.1 mg/kg body weight to approximately 100 mg/kg body weight. When administered to human, the agent of the present invention is administered preferably once a day, or preferably separately two to four times a day such that the administration is repeated at appropriate intervals.

Note that in a case where the drug of the present invention is used as a reagent for acylation, the reagent may comprise, as necessary, other ingredients acceptable as a reagent such as sterile water, a physiological saline, a buffer, and a preservative, in addition to the active ingredients. The reagent can be administered to a target (such as, for example, cells, fractions thereof, tissues, experimental animals) in accordance with the purpose to thereby acylate a chromosome protein.

EXAMPLE

Hereinafter, the present invention will be described more specifically on the basis of Example. However, the present invention is not limited to Example below.

[A. Materials and Methods]

1. Cell Fractionation

Approximately $10^6$ cells were detached from a culture dish by a trypsin treatment. After washed with PBS, the cell pellets were suspended in a cooled, cell lysis buffer [50 mM Tris (pH 7.5), 300 mMNaCl, 0.3% Triton X-100, protease inhibitor cocktail, and 1 mM PMSF], and placed on ice for 30 minutes. After the centrifugation (4° C., 1500 rpm, 2 minutes), the supernatant was collected as a cytoplasm fraction.

2. Western Blotting

Proteins were separated on a 4-20% SDS-PAGE gel, and transferred to a PVDF membrane, followed by blocking with 5% skim milk suspended in TBST for the reaction between the PVDF membrane and primary antibodies. The primary antibodies used were as follows.

Acetylated-lysine antibody (#9441, Cell Signaling), anti-acetyl Histone H4 (Lys77) (ABE186, Millipore), anti-acetyl Histone H2B (Lys120) (ab176430, Abcam), malonylated-lysine antibody (PTM-901, PTM Biolabs), glutarylated-lysine antibody (PTM-1151, PTM Biolabs), butyrylated-lysine antibody (PTM-301, PTM Biolabs), 2-hydroisobutyrylated antibody (PTM-801, PTM Biolabs), streptavidin-HRP (#3999S, Cell Signaling).

After washing with TBST, a secondary antibody (Anti-Rabbit IgG, HRP-linked, NA934V, GE) was reacted. The PVDF membrane was treated with a chemiluminescent detection reagent Luminata Forte Western HRP Substrate (Millipore), and the detection was performed using ImageQuant LAS 4000 (GE healthcare life sciences).

3. Comparison of Reactivity of Acetyl Group Donors

A buffer solution (50 mM HEPES, 150 mM NaCl, 0.01% Triton, pH 7.5) was added with a cytoplasm fraction (20%) and an acetyl group donor (1 mM), followed by reaction at room temperature for 10 hours. Thereafter, an anti-acetylated lysine antibody was used to perform western blotting.

4. Protein and Lysine Residue Selective Acylation Reaction

A buffer solution (20 mM Tris-HCl, pH 7.5) containing a reconstituted nucleosome (33 μg/mL 601 DNA) and a cytoplasm fraction (15%) was added with Ligand-DSH (2 to 5 μM), acyl CoA (1 mM), and TCEP (100 μM), followed by reaction at room temperature for 5 hours. Thereafter, western blotting was performed.

5. Yield Determination by LC-MS/MS and Exhaustive Analysis of Lysine Residue Selectivity (1) Sample Preparation Ligand-DSH (2 μM), acetyl CoA (1 mM), and TCEP (100 μM) were reacted in a buffer solution (20 mM Tris-HCl, pH 7.5) for 1 hour. After that, a reconstituted nucleosome (33 μg/mL 601 DNA) was added, followed by further reaction for 5 hours (final liquid amount 150 μL). Cooled trichloroacetic acid (30 μL) was added, and the resultant was placed on ice for 30 minutes. After the centrifugation (4° C., 15000 rpm, 5 minutes), the supernatant was removed. After further centrifugation (4° C., 15000 rpm, 1 minute), the supernatant was again removed. Cooled acetone (450 μL) was added. After the centrifugation (4° C., 15000 rpm, 5 minutes), the supernatant was removed. After further centrifugation (4° C., 15000 rpm, 1 minute), the supernatant was again removed. The above procedure was repeated once more. After drying was performed with a centrifugal evaporator for 10 minutes, MilliQ (89 μL), 10× DNase buffer (10 μL), and DNase I (1 μL, #2270A, Takara) were added, followed by reaction at 37° C. for 30 minutes. A 1M sulfuric acid (25 μL) was added and placed on ice for 1 hour, followed by centrifugation (4° C., 15000 rpm, 5 minutes), and the supernatant was collected. Centrifugation (4° C., 15000 rpm, 1 minute) was performed again to collect the supernatant to combine with the earlier supernatant. The resultant was added with acetone (500 μL), followed by sufficient stirring, and was placed overnight at −30° C. After the centrifugation (4° C., 15000 rpm, 5 minutes), the supernatant was removed. After further centrifugation (4° C., 15000 rpm, 1 minute), the supernatant was again removed. After drying was performed with a centrifugal evaporator for 10 minutes, an aqueous solution of ammonium bicarbonate (0.1 M, 20 μL) was added. The resultant was added with a mixture of propionic anhydride and methanol (1:3, 20 μL) prepared immediately before, further added with ammonia water (15 μL), and was placed at room temperature for 30 minutes. Drying was performed with a centrifugal evaporator for 75 minutes, followed by treatment with a digestive enzyme.

In the case of trypsin: an aqueous solution of ammonium bicarbonate (0.1M, 50 μL) and trypsin (1 μg) were added, followed by reaction at 37° C. for 21 hours.

In the case of chymotrypsin: 100 mM Tris-HCl, 10 mM CaCl$_2$ (50 μL, pH8.0), and chymotrypsin (8 μg) were added, followed by reaction at 25° C. for 21 hours.

A 5% aqueous solution of formic acid (25 μL) was added, followed by drying with a centrifugal evaporator for 75 minutes. The residue was dissolved in a 0.1% aqueous solution of formic acid (15 μL), and the resultant was used for LC-MS/MS.

(2) Setup of LC-MS/MS
AB Sciex Triple TOF 4600
Eksigent ekspert™ MicroLC 200
Column: 3C18-CL-120 (0.3 mm ID×150 mm)
Line gradient 2%-35% acetonitrile/0.1% formic acid, 25 minutes, 5 μL/min
Amount of Sample: 5 μL
ESI-Q-TOF MS, positive-ion mode.

(3) Method of Determining Yield

Figure 4:
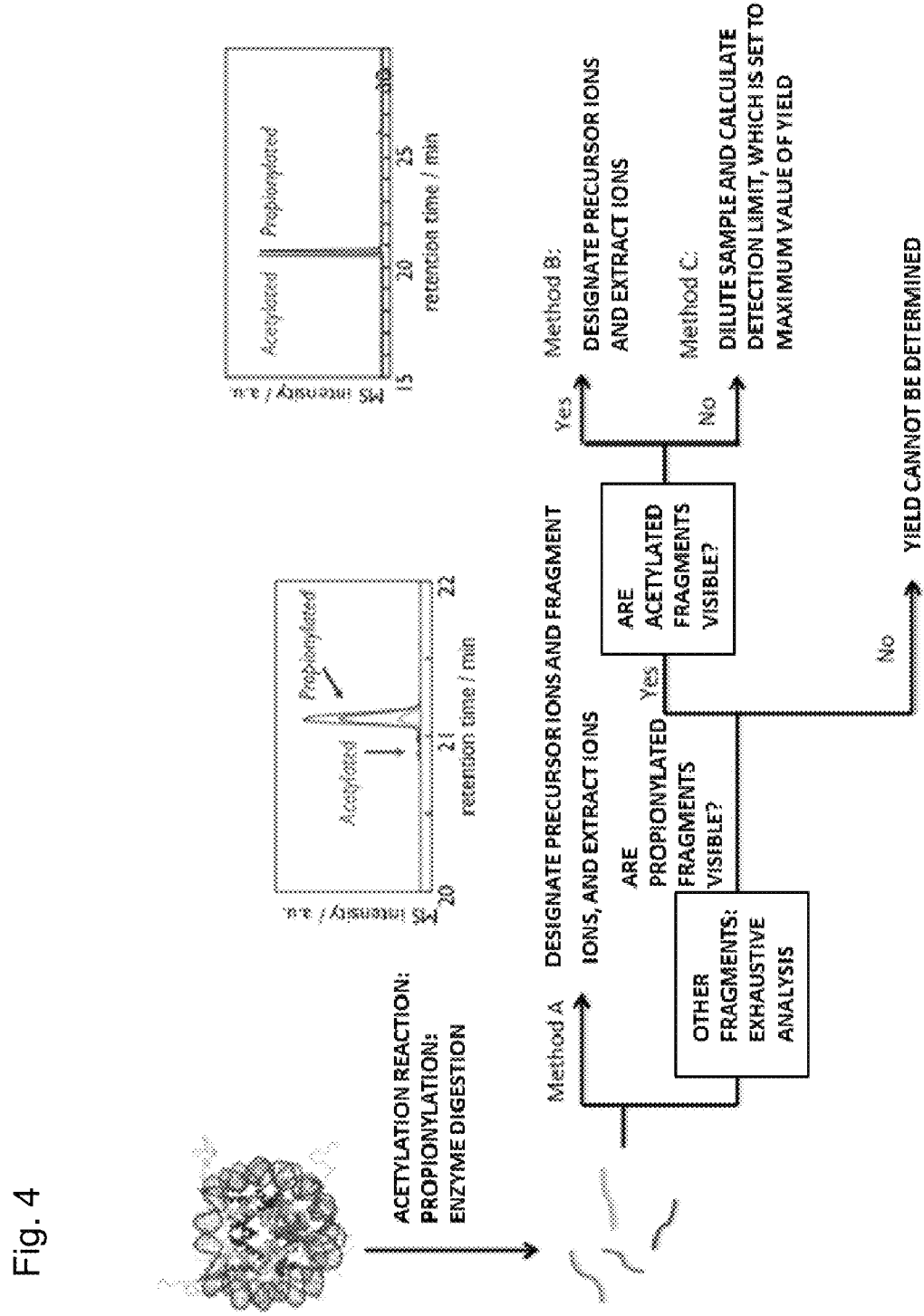
FIG. 4 is a diagram illustrating an overview of an exhaustive analysis of yield determination and lysine residue selectivity by LC-MS/MS.

An overview of a method of determining a yield is shown in FIG. 4.

Method A

Precursor ions are designated, and for each of the precursor ions, 2 to 4 MS/MS fragment ions having the highest strength were selected. Ion extraction (±0.5 Da) was performed for the designated precursor ions and the MS/MS fragment ions, and the yield was calculated in accordance with the equation below. This was carried out for all selected MS/MS fragments, and the final yield was determined as the average of the results.

yield (%)=[$A/A+P$]×100

(here, A represents a peak area of an acetylated peptide and P represents a peak area of a propionylated peptide)

If one peptide fragment includes three lysines, the yield of the central lysine was calculated as [yield in which acetylation has proceeded to one of the lysines at the ends—yield of the lysine at the extremity].

The used precursor ions and the fragment ions are as follows.

TABLE 1

| Residue | Digestive Enzyme | Peptide Fragment | Precursor Ion (Pr/Ac) | Fragment Ion |
|---|---|---|---|---|
| H2AK13 | Trypsin | 12-17 | 393.75/386.74 | $b_2, y_3, y_4$ |
| H2AK15 | Trypsin | 12-17 | 393.75/386.74 | $b_2, y_3, y_4$ |
| H2AK36 | Trypsin | 36-42 | 448.22/455.22 | $y_3, y_4, y_5, y_6$ |
| H2AK118 | Chymotrypsin | 116-123 | 594.82/587.81 | $b_3, y_6$ |
| H2AK119 | Chymotrypsin | 116-123 | 594.82/587.81 | $b_3, y_6$ |
| H2BK108 | Chymotrypsin | 107-121 | 586.65/581.98 | $b_3, b_5, b_7, b_9$ |
| H2BK106 | Chymotrypsin | 107-121 | 586.65/581.98 | $b_3, b_5, b_7, b_9$ |
| H2BK120 | Chymotrypsin | 107-121 | 586.65/581.98 | $b_{10}, y_2, y_3, y_5$ |
| H3K9 | Trypsin | 9-17 | 507.29/500.28 | $b_2, y_6, y_7, y_8$ |
| H3K14 | Trypsin | 9-17 | 507.29/500.28 | $b_2, y_6, y_7, y_8$ |
| H3K27 | Trypsin | 27-40 | 534.64/529.97 | $b_3, y_5, y_6, y_7$ |
| H3K36 | Trypsin | 27-40 | 534.64/529.97 | $b_3, y_5, y_6, y_7$ |
| H3K37 | Trypsin | 27-40 | 534.64/529.97 | $b_{10}, y_4$ |
| H3K56 | Trypsin | 54-63 | 653.87/646.86 | $b_3, y_6, y_7, y_8$ |
| H4K77 | Trypsin | 68-78 | 449.56/444.89 | $y_3, y_4, y_5, y_6$ |

Method B

For a chromatogram obtained by performing measurement in an Information Dependent Acquisition Mode, the yield was determined in accordance with the following equation from the peak area subjected to ion extraction (±0.5 Da) after designating the precursor ions.

yield (%)=[$A/A+P$]×100

(here, A represents a peak area of an acetylated peptide and P represents a peak area of a propionylated peptide)

Method C

For a chromatogram obtained by performing measurement in an Information Dependent Acquisition Mode, a propionylated peptide fragment was observed, but an acetylated peptide fragment was not observed. For this reason, the sample was diluted to calculate the detection limit of the propionylated peptide fragment, and estimation was carried out assuming that the acetylation yield was equal to or less than the detection limit.

(4) Synthesis

[Chem. 6]

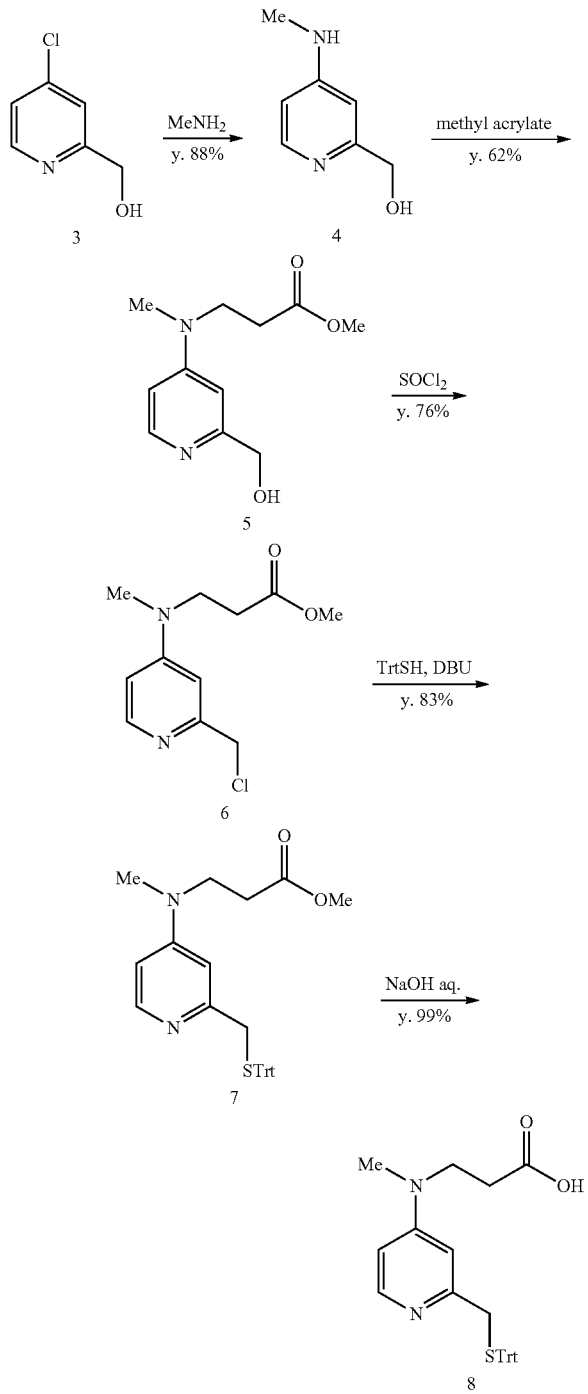

(4-(Methylamino)pyridin-2-yl) methanol (4)

Compound 3 (2.30 g, 16.0 mmol) was dissolved into a 12 M aqueous solution of methylamine (26.7 ml), followed by heating at 120 degrees for 18 hours in the ampoule. The solvent was depressurized and removed by distillation. Thereafter, the residue was dissolved into a solution of methylene chloride/methanol (4/1), and potassium carbonate (5 g) was added, followed by stirring for 4 hours. The potassium carbonate was removed by filtration, and the filtrate was concentrated. Thereby, Compound 4 (2.01 g, 14.5 mmol, 88% yield) was obtained.

$^1$H NMR (CD$_3$OD, 400 MHz) δ 7.90 (d, J=6.2 Hz, 1H), 6.67 (d, J=2.8 Hz, 1H), 6.38 (dd, J=2.8, 6.2 Hz, 1H), 4.51 (s, 2H), 2.80 (s, 3H); $^{13}$C NMR (CD$_3$OD, 100 MHz) δ 161.7, 157.7, 148.9, 106.6, 104.3, 65.4, 29.2; ESI-MS m/z 139 [M+H]$^+$.

Methyl 3-((2-(hydroxymethyl)pyridin-4-yl)(methyl) amino)propanoate (5)

Compound 4 (1.38 g, 10.0 mmol) was dissolved into methyl acrylate (22.5 ml), followed by heating at 80 degrees for 18 hours. The solvent was depressurized and removed by distillation. Thereafter, purification was performed by silica gel column chromatography (ethyl acetate/methanol=1/0 to 0/1). Thereby, Compound 5 (1.39 g, 6.20 mmol, 62% yield) was obtained.

$^1$H NMR (CD$_3$OD, 400 MHz) δ 7.96 (d, J=6.2 Hz, 1H), 6.77 (d, J=2.8 Hz, 1H), 6.51 (dd, J=2.8, 6.2 Hz, 1H), 4.52 (s, 2H), 3.71 (t, J=7.3 Hz, 2H), 3.61 (s, 3H), 2.98 (s, 3H), 2.58 (t, J=7.3 Hz, 2H); $^{13}$C NMR (CD$_3$OD, 100 MHz) δ 173.8, 161.8, 155.9, 149.1, 106.5, 104.1, 65.4, 52.3, 48.2, 37.9, 32.4; ESI-MS m/z 225 [M+H]$^+$.

Methyl 3-((2-(chloromethyl)pyridin-4-yl)(methyl) amino)propanoate (6)

Compound 5 (640 mg, 2.85 mmol) was dissolved into methylene chloride (14.0 ml), and thionyl chloride (0.311 ml, 4.28 mmol) was slowly added dropwise thereto. After stirring at room temperature for 10 hours, an aqueous solution of potassium carbonate was added with caution. The aqueous layer was extracted with methylene chloride, the organic layer was concentrated, and the residue was purified by silica gel chromatography (ethyl acetate/methanol=1/0 to 0/1). Thereby, Compound 6 (529 mg, 2.18 mmol, 76% yield) was obtained.

$^1$H NMR (CD$_3$OD, 500 MHz) δ 8.04 (d, J=6.3 Hz, 1H), 6.80 (d, J=2.3 Hz, 1H), 6.61 (dd, J=2.3, 6.3 Hz, 1H), 4.54 (s, 2H), 3.75 (t, J=6.9 Hz, 2H), 3.65 (s, 3H), 3.02 (s, 3H), 2.62 (t, J=6.9 Hz, 2H); $^{13}$C NMR (CD$_3$OD, 100 MHz) δ 173.8, 157.6, 156.0, 149.7, 109.0, 107.5, 52.3, 48.2, 47.4, 37.9, 32.4; ESI-MS m/z 243 [M+H]$^+$.

Methyl 3-(methyl(2-((tritylthio)methyl)pyridin-4-yl) amino)propanoate (7)

Compound 6 (922 mg, 3.80 mmol) was dissolved into methylene chloride (19.0 ml), and TrtSH (1.58 g, 5.72 mmol) and DBU (0.852 ml, 5.70 mmol) were added thereto, followed by stirring at room temperature for 10 hours. An aqueous solution of potassium carbonate was added with caution. The aqueous layer was extracted with methylene chloride, the organic layer was concentrated, and the residue was purified by silica gel chromatography (ethyl acetate/hexane=1/1 to ethyl acetate/methanol=20/1). Thereby, Compound 7 (1.53 g, 3.17 mmol, 83% yield) was obtained.

$^1$H NMR (CD$_3$OD, 500 MHz) δ 7.90 (d, J=6.3 Hz, 1H), 7.40-7.38 (m, 6H), 7.22-7.19 (m, 6H), 7.14-7.11 (m, 3H), 6.38 (dd, J=2.3, 6.3 Hz, 1H), 6.08 (d, J=2.3 Hz, 1H), 3.56 (s, 3H), 3.51 (t, J=6.9 Hz, 2H), 3.33 (s, 2H), 2.78 (s, 3H), 2.43 (t, J=6.9 Hz, 2H); $^{13}$C NMR (CD$_3$OD, 125 MHz) δ 173.5, 158.1, 155.3, 149.4, 145.9, 130.8, 129.0, 127.9, 107.1, 106.4, 68.6, 52.3, 48.0, 39.6, 37.8, 32.3; ESI-MS m/z 483 [M+H]⁺.

3-(Methyl(2-((tritylthio)methyl)pyridin-4-yl)amino) propanoic acid (8)

Compound 7 (1.45 g, 3.00 mmol) was dissolved into methanol (15 ml) and a 2 M aqueous solution of sodium hydroxide (7.50 ml, 15.0 mmol) was added thereto, followed by stirring at room temperature for 3 hours. Neutralization was performed with a 1 M hydrochloric acid to remove the solvent by distillation, followed by purification by silica gel chromatography (ethyl acetate/methanol=4/1 to 1/2). Thereby, Compound 8 (1.39 g, 2.97 mmol, 99% yield) was obtained.

¹H NMR (CD₃OD, 500 MHz) δ 7.79 (d, J=6.9 Hz, 1H), 7.36-7.34 (m, 6H), 7.24-7.20 (m, 6H), 7.17-7.13 (m, 3H), 6.58 (dd, J=2.7, 6.9 Hz, 1H), 6.08 (d, J=2.7 Hz, 1H), 3.60 (t, J=6.9 Hz, 2H), 3.51 (s, 2H), 2.94 (s, 3H), 2.34 (t, J=6.9 Hz, 2H); ¹³C NMR (CD₃OD, 100 MHz) δ 179.1, 156.9, 154.7, 145.6, 144.3, 130.8, 129.1, 128.1, 107.2, 106.5, 68.8, 50.4, 38.2, 37.0, 35.8; ESI-MS m/z 469 [M+H]⁺.

[Chem. 7]

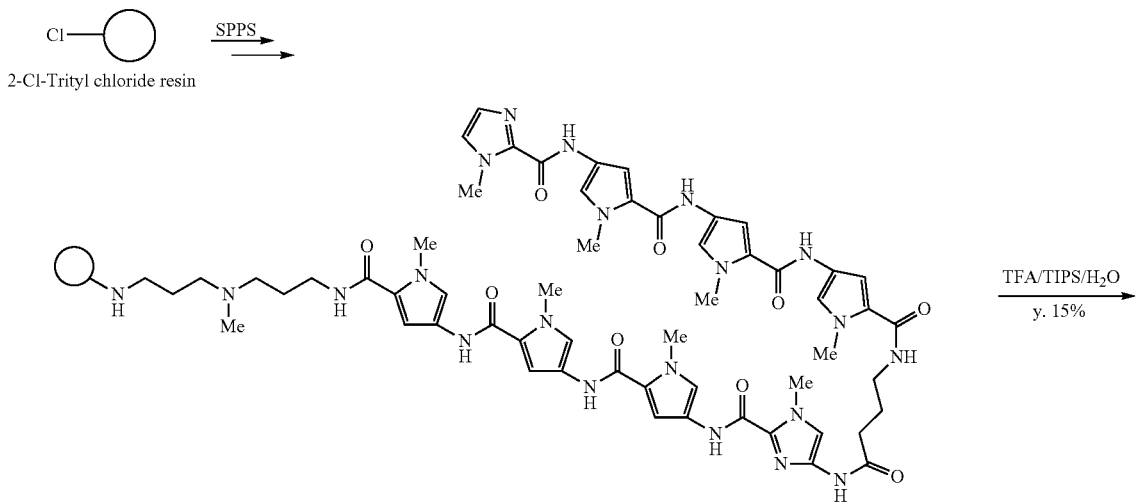

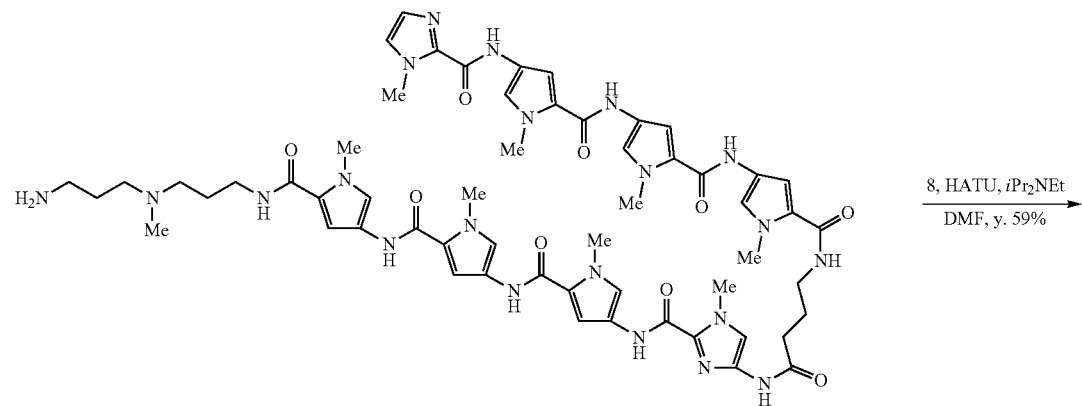

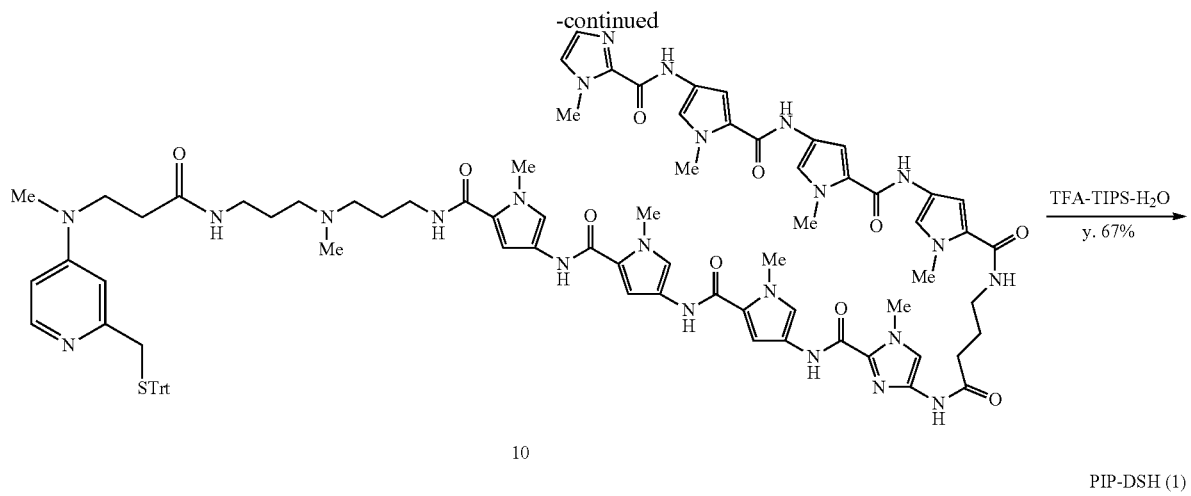

PIP-DSH (1)

PIP-amine (9)

HATU and iPr$_2$NEt were used as condensation agents, and 1-Methyl-1H-imidazole-2-carboxylic acid, 4-Amino-1-methyl-1H-pyrrole-2-carboxylic acid, and 4-[(9-Fluorenyl-methoxycarbonyl)amino]butanoic acid were used as building blocks. Thereby, a PIP chain was elongated on a 2-Chlorotrityl chloride resin (100 mg, 1.3 mmol/g, 0.133 mmol) in accordance with a normal Fmoc-peptide solid-phase synthesis method. Cutout from the resin was performed with TFA/TIPS/H$_2$O (95/2.5/2.5), and purification was performed with HPLC (10% acetonitrile/0.1% TFA aqueous solution→line gradient 10-100% 40 minutes, flow: 10 ml/min, 230 nm, YMC-Pack ODS-AM: 20 mm ID×250 mm). Thereby, PIP-amine (9, 31.4 mg, 0.0204 mmol, 15% yield) was obtained.

MALDI-TOF MS m/z Calcd: 1193.57 [M+H]$^+$, Found: 1193.48. retention time: 19.9 minutes.

PIP-DSTrt (10)

PIP-amine (15.4 mg, 0.0100 mmol) was dissolved into DMF (0.18 ml), and 8 (23.4 mg, 0.0500 mmol), HATU (19.0 mg, 0.0500 mmol), and iPr$_2$Net (0.0200 ml, 0.115 mmol) were added thereto, followed by stirring at room temperature for 9 hours. After the reaction liquid was concentrated, purification was performed with HPLC (10% acetonitrile/0.1% TFA aqueous solution→line gradient 10-100% 40 minutes, flow: 10 ml/min, 230 nm, YMC-Pack ODS-AM: 20 mm ID×250 mm). Thereby, PIP-DSTrt (10, 11.7 mg, 0.00587 mmol, 59% yield) was obtained.

MALDI-TOF MS m/z Calcd: 1643.75[M+H]$^+$, Found: 1643.88. retention time: 26.1 minutes.

PIP-DSH (1)

PIP-DSTrt (11.7 mg, 0.00580 mmol) was added with MilliQ water (20 μl) and TFA (0.160 ml), followed by stirring at room temperature for 30 minutes. After the reaction liquid was concentrated, purification was performed with HPLC (10% acetonitrile/0.1% TFA aqueous solution-→line gradient 10-100% 40 min, flow: 10 ml/min, 230 nm, YMC-Pack ODS-AM: 20 mm ID×250 mm). Thereby, PIP-DSH (1, 6.85 mg, 0.00393 mmol, 67% yield) was obtained.

MALDI-TOF MS m/z Calcd: 1401.64 [M+H]$^+$, Found: 1401.76. retention time: 22.3 minutes.

[Chem. 8]

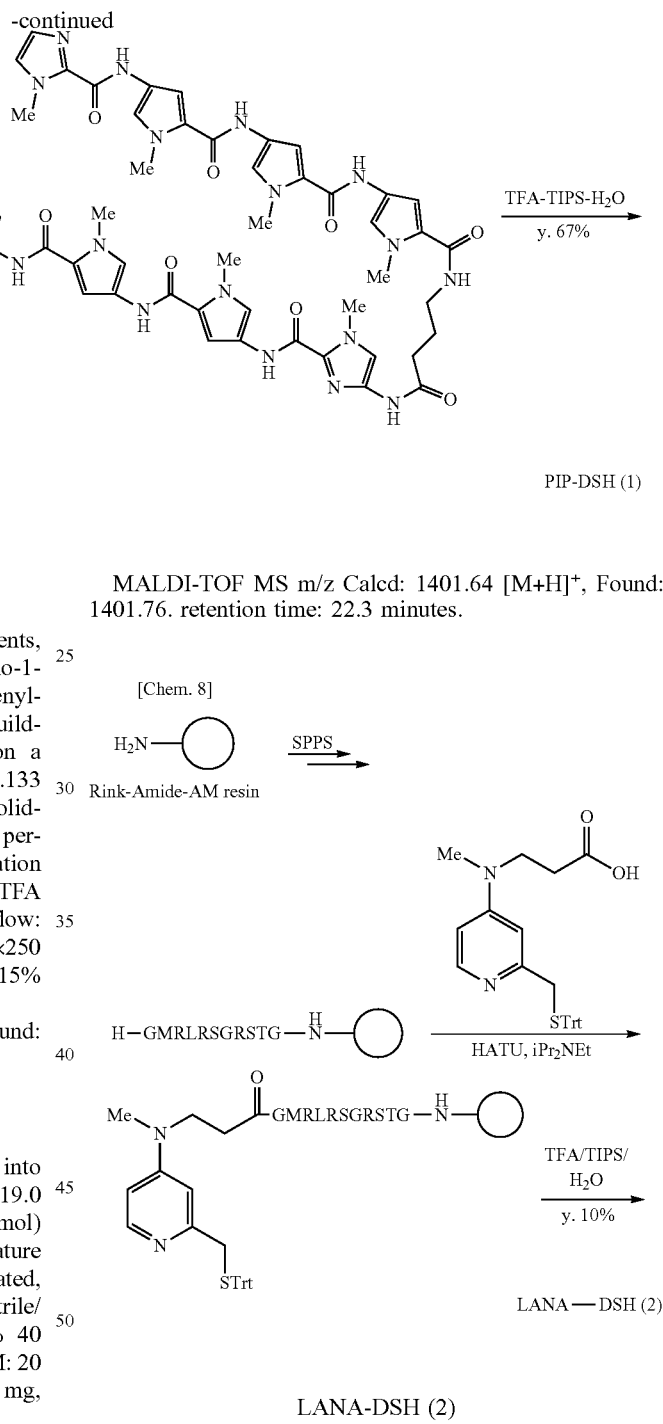

LANA-DSH (2)

DIC and HOBt were used as condensation agents. Thereby, H-GMRLRSGRSTG—was synthesized on a Rink-Amide-AM resin (75.3 mg, 0.73 mmol/g, 0.055 mmol) in accordance with a normal Fmoc-peptide solid-phase synthesis method. Compound 8 was condensed at an N-terminus by using HATU and iPr$_2$NEt, and thereby protection LANA-DSH was synthesized in the form of resin. Deprotection and cutout were performed with TFA/TIPS/H$_2$O (95/2.5/2.5), and purification was performed with HPLC (line gradient; 0-75% acetonitrile/0.1% TFA aqueous solution, flow: 7 ml/min, 30 minutes, 254 nm, YMC-Pack ODS-AM: 20 mm ID×250 mm). Thereby, LANA-DSH (2, 10.5 mg, 0.00570 mmol, 10% yield) was obtained.

ESI-MS m/z Calcd: 346.9[M+4H]$^{4+}$, Found: 347.0. retention time: 28.2 minutes.

[B. Results]

First, the reactivity of the acetylating agent used was studied (FIG. 1). Several types of acetylating agents (FIG. 1A) were mixed with cytoplasm fractions acquired from living cells, followed by western blotting using an acetylation lysine antibody. The results revealed that while EG5-PTA and NMD non-selectively acetylated a large quantity of protein, acetyl CoA, which is an acetyl group donor used by organisms, and its analog TEG-Ac did not cause such non-selective acetylation (FIG. 1B).

The results described above mean that construction of a catalyst system with high selectivity is possible if a catalyst can be developed which is capable of activating a low reactivity acetyl group donor with suppressed non-selective reaction such as acetyl CoA.

The structure of the novel catalyst DMAP-SH (DSH) developed this time is illustrated in FIG. 2A, and an expected acetyl CoA activation mechanism is illustrated in FIG. 2B. Although DMAP cannot activate acetyl CoA, the novel catalyst DMAP-SH takes the acetyl groups in the catalyst molecules when newly introduced thiol groups and thioester groups of acetyl CoA cause thiol-thioester exchange reaction, thereby activating the acetyl groups through an intramolecular reaction. Here, by selecting an appropriate R-group, it was considered that the target protein could be acetylated with high selectivity.

The present Example selected PIP (Dervan, P. B., Bioorganic & Medicinal Chemistry 2001, 9, 2215-2235) as a DNA sequence specifically recognizing binding molecule, and LANA (Barbera, A. J. et al., Science 2006, 311, 856-861) as a histone protein binding molecule. Each of them was linked with DMAP-SH and the molecule was used as a catalyst.

Figure 3:
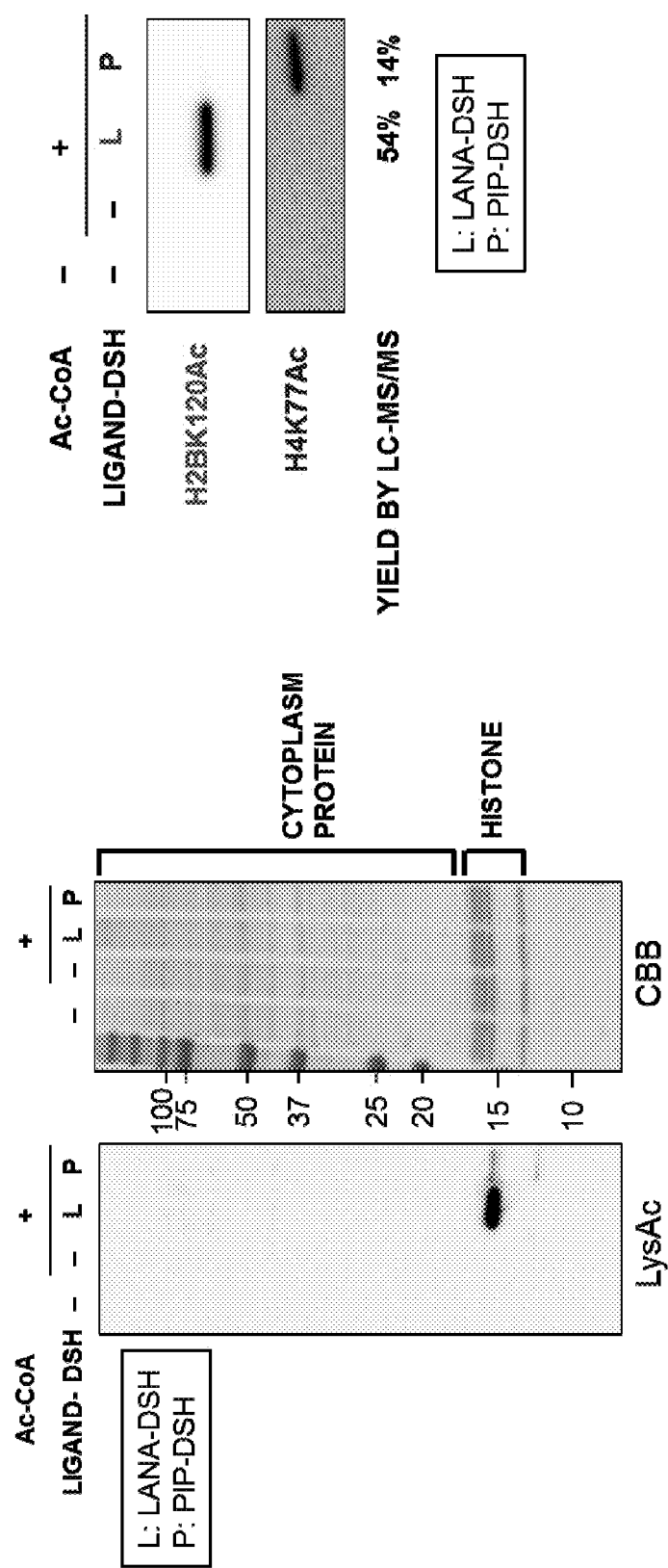
FIG. 3 is a diagram illustrating results of analyzing an ability of a reconstituted nucleosome to acetylate by catalysts (PIP-DSH and LANA-DSH) of the present invention. "A" is a photo indicating results of detecting protein selective acetylation, and "B" is a photo indicating results of detecting lysine residue selective acetylation.

First, protein selectivity was evaluated. A reconstituted nucleosome prepared in accordance with a known method (Tachiwana, H. et al., Proceedings of the National Academy of Sciences of the United States of America 2010, 107, 10454-10459) and cytoplasm fractions acquired from living cells were mixed. Then, evaluation was carried out on whether or not the newly developed catalyst could selectively acetylate histones by western blotting using an acetylation lysine antibody (FIG. 3A). As a result, as in the earlier experiment, while acetylation did not proceed when only acetyl CoA was used, histone-selective acetylation was achieved by using LANA-DSH or PIP-DSH. Note that when an experiment was carried out using a molecule having the following structure formed by partially cutting out acetyl CoA, histone-selective acetylation was observed in the same way.

[Chem. 9]

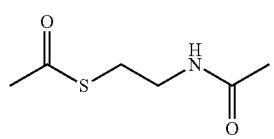

Next, the selectivity of lysine residues in histones was evaluated. A similar reaction was evaluated by western blotting using a residue-selective acetylation lysine antibody. It was revealed that H2BK120 was strongly acetylated in LANA-DSH and H4K77 was strongly acetylated in PIP-DSH (FIG. 3B).

Figure 8:
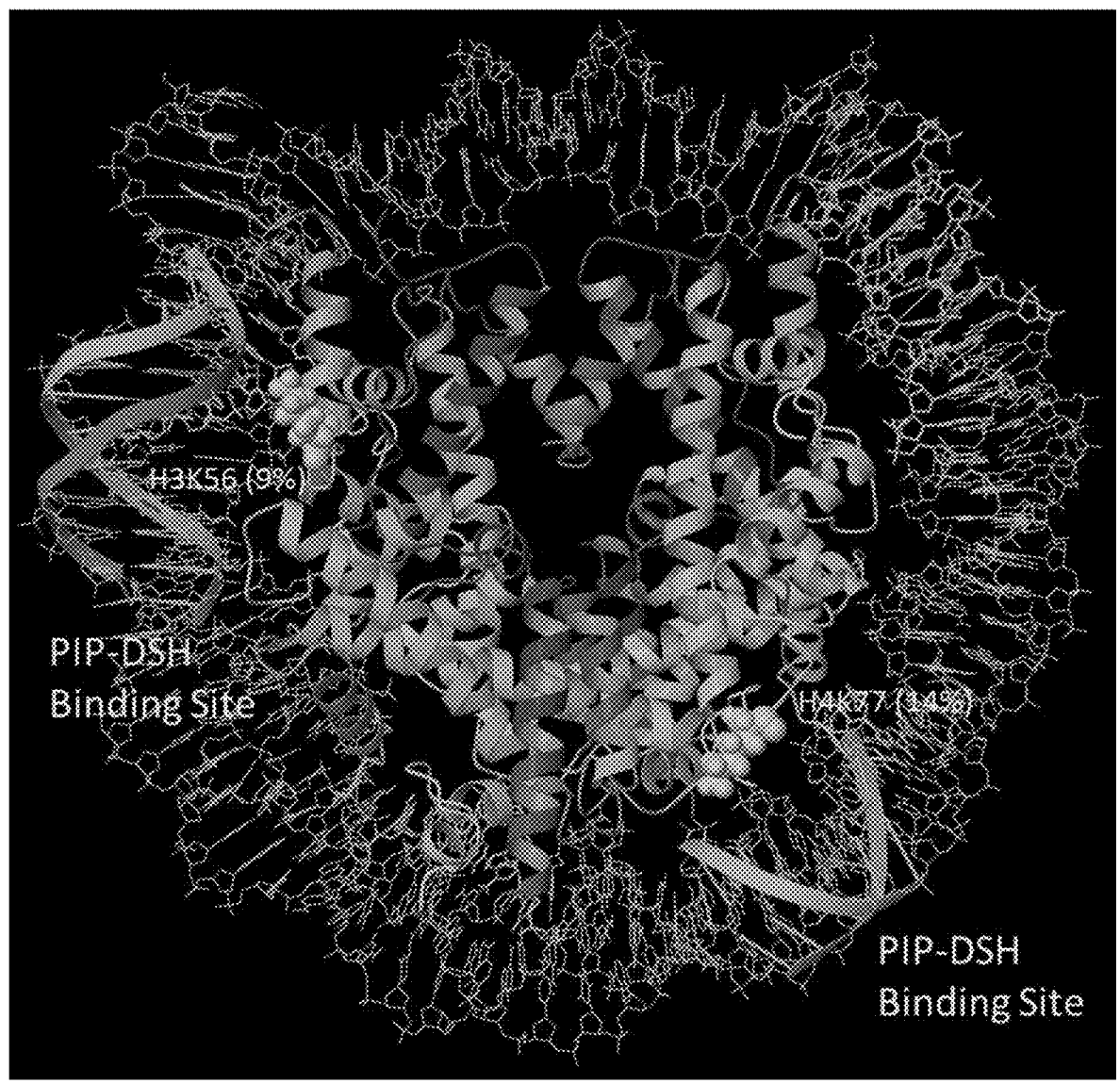
FIG. 8 is a diagram illustrating an X-ray crystal structure indicating localization of the catalyst (PIP-DSH) of the present invention on the nucleosome. This localization was predicted from the sequence of PIP.

The reacted nucleosome was treated with a digestive enzyme for the purposes of determining the reaction yield and investigating the residue selectivity in further detail. The produced peptide fragments were analyzed by LC-MS/MS (FIGS. 5 and 6). As a result, in the case of using LANA-DSH, H2BK120 was acetylated at a yield of 54% and it was revealed that the lysine residue selectivity was extremely high (FIG. 5). In the case of using PIP-DSH, H3K36 was acetylated at a yield of 14%, H3K56 at 9%, and H4K77 at 14%, and it was revealed that the lysine residue selectivity was high in the same way (FIG. 6). These results were backed up reasonably from the X-ray crystal structure. To be more specific, while LANA is known to bind to an H2A-H2B dimer (Barbera, A. J. et al., Science 2006, 311, 856-861), H2BK120 acetylated with the present catalyst system was positioned near the catalyst position expected from the co-crystalline structure of the LANA and the nucleosome (FIG. 7). Similarly, DNA binding sites of PIP-DSH expected from the sequence of PIP used and the crystalline structure of the nucleosome (Vasudevan, D., Chua, E. Y. D. & Davey, C. A., Journal of Molecular Biology 2010, 403, 1-10) were positioned near acetylated H3K56 and H4K77 (FIG. 8). These results indicate that it is possible to highly selectively acetylate the target lysine residue depending on the ligand by introducing an appropriate ligand into the developed catalyst. In other words, structure-based logical design is possible.

PIP in particular can freely select the target DNA sequence by appropriately designing its sequence. Hence, use of PIP may make it possible to freely position a lysine (Tropberger, P. & Schneider, R., Nature Structural & Molecular Biology 2013, 20, 657-661) for acetylation located in a DNA-histone interaction site, which is known to greatly affect the structure of a nucleosome.

Recently, it has been revealed that acylation other than acetylation takes place in histones, which has been drawing attention. However, almost all of the functions have not yet been understood, which is a recent important issue in epigenetics (Kebede, A. F., Schneider, R. & Daujat, S., Febs Journal 2015, 282, 1658-1674). Thus, a method which can position-selectively introduce acylation into histones is expected to be a strong tool to advance the investigation of the functions.

In light of the above, a study was carried out on whether or not acylation other than acetylation would be possible using the developed catalyst. As a result, it was revealed that use of LANA-DSH and various acyl CoA enabled malonylation (Non Patent Literature 5), glutarylation (Non Patent Literature 6), butyrylation (Non Patent Literature 7), 2-hydroxy-iso-butyrylation (Non Patent Literature 8), and biotinylation (Non Patent Literature 9) (FIG. 9).

INDUSTRIAL APPLICABILITY

An artificial catalyst system of the present invention enables various selective acylation simply by changing acyl group donors to be combined with a catalyst. In addition, it is possible to perform highly selective acylation with various sites as targets only by changing molecules which are to be introduced into the catalyst and which have binding ability to a target acylation area. Hence, it can be said that the present invention is a system highly versatile and excellently practical.

In addition, the artificial catalyst system of the present invention based on the concept of catalysis medicine is applicable to various reactions with which in vivo enzymes are involved. Particularly in the case where a loss or inactivation of an in vivo enzyme is involved in a particular disease, the artificial catalyst system, which functions instead of the enzyme, makes it possible to treat the disease. Thus, the present invention can contribute vastly to the field of medical treatment.

The artificial catalyst system, which uses the combination of a target acylation area binding catalyst and acyl CoA or a derivative thereof, is applicable to, for example, the treatment of diseases attributed to the decrease in acetylation of chromosome proteins. In particular, the system is highly useful for diseases attributed to the inactivation of histone acetyltransferase for which it is difficult for conventional histone deacetylase inhibitors to exhibit their efficacies.

The present invention has succeeded in establishing a novel artificial catalyst system which is based on the concept of catalysis medicine, and paves the way toward new medical treatment essentially different from the conventional concept of medical treatment which adjusts the functions of endogenous enzymes.

The invention claimed is:
1. A compound comprising the following structure:

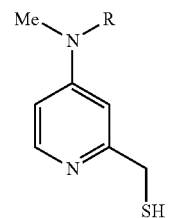

wherein R represents any molecule having binding ability to a target acylation area.

2. A drug for acylation of a protein, comprising a combination of the compound according to claim 1 and acyl CoA or a derivative thereof.

* * * * *